US005750740A

United States Patent [19]

Jones et al.

[11] Patent Number: 5,750,740
[45] Date of Patent: May 12, 1998

[54] PROCESS FOR PREPARING EPOXIDES FROM CARBONYL COMPOUNDS USING SULPHONIUM OR SULPHOXONIUM YLIDES AND INTERMEDIATES USEFUL THEREIN

[75] Inventors: Raymond Vincent Heavon Jones, West Lothian; Elizabeth Shearer Currie Simpson, Lanarkshire, both of Scotland

[73] Assignee: Zeneca Limited, London, England

[21] Appl. No.: 451,936

[22] Filed: May 25, 1995

Related U.S. Application Data

[62] Division of Ser. No. 98,379, Aug. 10, 1993, Pat. No. 5,637,727.

[30] Foreign Application Priority Data

Feb. 15, 1991 [GB] United Kingdom ............... 9103260

[51] Int. Cl.$^6$ ............... C07D 301/02; C07C 381/00; C07C 381/12
[52] U.S. Cl. ............................. 549/519; 568/18
[58] Field of Search ....................... 549/519; 568/18

[56] References Cited

U.S. PATENT DOCUMENTS

| | | | |
|---|---|---|---|
| 2,316,152 | 4/1943 | Bearse et al. | 568/18 X |
| 2,768,990 | 10/1956 | De Jong et al. | 568/18 |
| 3,187,008 | 6/1965 | Baird et al. | 568/18 |
| 3,442,912 | 5/1969 | Hatch | 549/519 |
| 3,455,967 | 7/1969 | Hatch | 549/519 |
| 3,462,462 | 8/1969 | Hatch | 549/519 |
| 3,998,856 | 12/1976 | Rosenberger | 549/519 X |
| 4,632,999 | 12/1986 | Zerbes et al. | 549/519 |
| 4,886,892 | 12/1989 | Zerbes et al. | 549/519 |
| 4,898,954 | 2/1990 | Mohrmann et al. | 549/519 |
| 4,929,735 | 5/1990 | Reiser et al. | 548/268.8 |
| 4,960,911 | 10/1990 | Zerbes et al. | 549/519 |
| 4,988,829 | 1/1991 | Fiedler et al. | 549/519 |
| 4,992,565 | 2/1991 | Mohrmann et al. | 549/519 |
| 5,256,802 | 10/1993 | Macke et al. | 549/519 |

FOREIGN PATENT DOCUMENTS

| | | |
|---|---|---|
| 254032 | 11/1988 | Czechoslovakia . |
| 0094726 | 11/1983 | European Pat. Off. . |
| 0205400 | 12/1986 | European Pat. Off. . |
| 0219799 | 4/1987 | European Pat. Off. ............... 549/519 |
| 840778 | 1/1939 | France . |
| 3733755 | 4/1989 | Germany ............... 549/519 |
| 52-68111 | 6/1977 | Japan . |
| 53-84952 | 7/1978 | Japan . |

OTHER PUBLICATIONS

Bosansky et al. Chemical Abstracts, vol. 111, #57525q (1989).
Ray et al., "Sulfonium Compounds. III. The Reaction of Organic Sulfides with Organic Sulfates," Journal of Organic Chemistry, vol. VIII, 391–396 (1943).
Borredon et al., Tetrahedron Letters, vol. 23, pp. 5283–5286 (1982).
Reid, "Organic Chemistry of Bivalent Sulfur," vol. II, pp. 64–65 (1960).
Badet, Bernard et al., "Preparation Aisee de Sels de Sulfonium," Tetrahedron Letters No. 13, pp. 1101–1104 (1979).
Badet, Bernard et al., "On the Stereochemistry of Sulphonium Salts Formation by Reaction of Thioethers with Alcohols or Ethers in Acid Medium." Tetrahedron, vol. 37, pp. 887–890 (1981).
Milligan, Terry W. Et al., "A Direct Synthesis of Sulfonium Perchlorates," J. Org. Chem., vol. 28, pp. 235–236 (1963).
Haas, Otto et al., "Tribenzylsulfonium Hydrogen Sulfate and Hydroxide," J. Am. Chem. Soc., vol. 65, pp. 1238–1239 (1943).
Fichter et al., "Die elektrolytische Oxydation aromatischer Sulfide," Chem. Ber., vol. 43, pp. 3422–3429 (1910).
Rosenberger, Michael et al."The Synthesis of $\beta,\mu$– and $\alpha,\beta$–Unsaturated Aldehyde Aldehydes via Polyene Epoxides" Helvetica Chim Acta, vol. 63, pp. 1665–1674 (1980).
Chemical Abstract 34, 6388, (1940), ref. Dutch Patents 47,897 and 47,715, Van Peski et al.
Chemical Abstract 34, 3848, (1940), ref. Canadian Patent 388,120 Van Peski et al.

*Primary Examiner*—Floyd D. Higel
*Attorney, Agent, or Firm*—Marian T. Thomson

[57] ABSTRACT

A process for transforming a carbonyl compound into its corresponding epoxide, which comprises contacting the carbonyl compound with either trimethylsulphonium hydrogen sulphate and/or bis(trimethylsulphonium) sulphate or trimethylsulphoxonium hydrogen sulphate and/or bis (trimethylsulphoxonium) sulphate, in the presence of a base.

8 Claims, No Drawings

PROCESS FOR PREPARING EPOXIDES FROM CARBONYL COMPOUNDS USING SULPHONIUM OR SULPHOXONIUM YLIDES AND INTERMEDIATES USEFUL THEREIN

This application is a division of application Ser. No. 08/098,379, filed Aug. 10, 1993, now U.S. Pat. No. 5,637,727.

This invention relates to the preparation of epoxides from carbonyl compounds using either trimethylsulphonium hydrogen sulphate and/or bis(trimethylsulphonium) sulphate or trimethylsulphoxonium hydrogen sulphate and/or bis(trimethylsulphoxonium) sulphate. It also relates to trimethylsulphonium hydrogen sulphate, trimethylsulphoxonium hydrogen sulphate and bis(trimethylsulphoxonium) sulphate, which are novel compounds, and to processes for their preparation. The invention further relates to processes for preparation of sulphonium ylide, $(CH_3)_2S^+{-}^-CH_2$ and sulphoxonium ylide, $(CH_3)_2S^+(O){-}^-CH_2$ using these intermediates and a process for the preparation of fungicides and insecticides using these intermediates.

It is well known to prepare epoxides from carbonyl compounds using sulphonium or sulphoxonium salts. In particular, it is known to react dimethyl sulphide with dimethyl sulphate in an organic solvent, and then to contact the trimethylsulphonium methylsulphate so formed with a carbonyl compound in the presence of a strong base to form an epoxide. This epoxidation reaction is believed to proceed via the intermediate generation of the sulphonium ylide, $(CH_3)_2S^+{-}^-CH_2$ or sulphoxonium ylide, $(CH_3)_2S^+(O){-}^-CH_2$. A disadvantage of the known process is that organic material, in the form of an alkali metal methylsulphate, is present in the effluent. As well as being environmentally undesirable, methylating agent is lost and this is chemically inefficient. A further disadvantage is that dimethyl sulphate is a carcinogen.

According to the present invention there is provided a process for transforming a carbonyl compound into its corresponding epoxide, which comprises contacting the carbonyl compound with either trimethylsulphonium hydrogen sulphate and/or bis(trimethylsulphonium) sulphate or trimethylsulphoxonium hydrogen sulphate and/or bis (trimethylsulphoxonium) sulphate, in the presence of a base.

The compounds, trimethylsulphonium hydrogen sulphate having the formula: $(CH_3)_3S^+.HSO_4^-$, trimethylsulphoxonium hydrogen sulphate having the formula: $(CH_3)_3S(O).HSO_4$, and bis(trimethylsulphoxonium) sulphate having the formula: $((CH_3)_3S(O).)_2SO_4$, are novel and form another aspect of the present invention.

The compound, trimethylsulphonium hydrogen sulphate, is a novel compound. Although it is mentioned by name in Czechoslovakian Patent No 254,032, no method or reference is given for its preparation.

Therefore, according to yet another aspect of the present invention, there is provided a process for preparing trimethylsulphonium hydrogen sulphate which comprises reacting together dimethylsulphide, methanol and sulphuric acid at a temperature of from −20° C. to +100° C. (in a sealed system) or from −20° C. to +40° C. (at atmospheric pressure).

Suitably, from 1 to 10 moles of dimethylsulphide, normally about 2 moles, and from 1 to 10 moles of sulphuric acid, normally from 1 to 2 moles, are used for each mole of methanol. The dimethyl sulphide, before it is consumed in the reaction, and any excess used will act as a solvent. Excess sulphuric acid will require to be neutralised at the epoxidation stage by the addition of extra base.

In a typical preparation, the methanol is added slowly, for example dropwise, to a molar excess of dimethyl sulphide, for instance, 2 moles of dimethyl sulphide for each mole of methanol used in the reaction, at a temperature preferably below 25° C., when the reaction is carried out at atmospheric pressure. Concentrated sulphuric acid such as commercially available 98% sulphuric acid solution, may then be added gradually to the stirred mixture maintaining the temperature below 25° C. The time taken for the reaction will depend inter alia on its scale. Where half a mole of methanol (i.e. 16 g) is used, the methanol addition is completed typically in about ten minutes, and the sulphuric acid addition in about twenty minutes. Alternatively, the methanol may be added to a mixture of the sulphuric acid and dimethyl sulphide. The reaction mixture may be stirred for several hours at ambient temperature before use.

In an alternative method of preparation, which the invention also provides, trimethylsulphonium hydrogen sulphate is prepared by a process which comprises reacting together dimethyl sulphide, trimethylsulphonium methyl sulphate and sulphuric acid at temperature of from −20° C. to +100° C. (in a sealed system) or from −20° C. to +40° C. (at atmospheric pressure).

This reaction is conveniently carried out by adding a molar excess of dimethyl sulphide, for example, 2 moles of dimethyl sulphide for each mole of trimethylsulphonium methyl sulphate used in the reaction, to an aqueous solution of trimethylsulphonium methyl sulphate and then adding gradually to the mixture about 2 moles of concentrated sulphuric acid, such as 98% sulphuric acid. The reaction mixture is then heated to about 40° C., when the reaction is carried out at atmospheric pressure, and stirred for several hours until reaction is complete. Trimethylsulphonium methyl sulphate is a known compound and may be prepared by the reaction of dimethyl sulphide and dimethyl sulphate.

In another method of preparation, trimethylsulphonium hydrogen sulphate is prepared by a process which comprises reacting together a trimethylsulphonium halide, sulphuric acid and hydrogen peroxide at a temperature of from 0° C. to 100° C.

Trimethylsulphoxonium hydrogen sulphate can also be prepared using this process therefore, according to a further aspect of the present invention there is provided a process for preparing trimethylsulphoxonium hydrogen sulphate which comprises reacting together trimethylsulphoxonium halide, sulphuric acid and hydrogen peroxide at a temperature of from 0° C. to 100° C.

This reaction is conveniently carried out by adding, with stirring, an aqueous mixture of about one mole of concentrated sulphuric acid, such as 98% sulphuric acid, and about a half mole of hydrogen peroxide, such as 30% hydrogen peroxide, to one mole of, for example, trimethylsulphonium iodide, in the presence of an inert, water immiscible, iodine-extracting solvent, such as carbon tetrachloride, in this case to remove iodine produced during the reaction. If using trimethylsulphonium chloride, the liberated chlorine can be removed using a sodium hydroxide scrubber, suitably with an inert gas flow. If using the bromide, either a bromine-extracting solvent or scrubber can be used. The trimethylsulphonium hydrogen sulphate so formed can be isolated from the aqueous phase by evaporation after the unreacted peroxide has been destroyed by the addition of, for example, palladium on carbon. The trimethylsulphonium halide in this preparation can be replaced by trimethylsulphoxonium halide for the preparation of trimethylsulphoxonium hydrogen sulphate.

Trimethylsulphonium and trimethylsulphoxonium halides are readily prepared using processes known in the art, for example, Organic Chemistry of Sulfur, pages 474–475, edited by S. Oae, 1977; Kuhn and Trischmann, Annales 611, page 117, (1958).

The invention further includes the products obtained by the processes of the invention.

In a further aspect there is provided a process for preparing sulphonium ylide $(CH_3)_2S^+\text{—}^-CH_2$ using trimethylsulphonium hydrogen sulphate which comprises either (a) reacting together dimethyl sulphide, methanol and sulphuric acid at a temperature of from $-20°$ C. to $+100°$ C. (in a sealed system) or from $-20°$ C. to $+40°$ C. (at atmospheric pressure); or (b) reacting together dimethyl sulphide, trimethylsulphonium methyl sulphate and sulphuric acid at a temperature of from $-20°$ C. to $+100°$ C. (in a sealed system) or from $-20°$ C. to $+40°$ C. (at atmospheric pressure); or (c) reacting together a trimethylsulphonium halide, sulphuric acid and hydrogen peroxide at a temperature of from $0°$ C. to $100°$ C.; and basification of the trimethylsulphonium hydrogen sulphate formed.

Yet further there is provided a process for preparing sulphoxonium ylide $(CH_3)_2S_+(O)\text{—}^-CH_2$ using trimethylsulphoxonium hydrogen sulphate which comprises reacting together a trimethylsulphoxonium halide, sulphuric acid and hydrogen peroxide at a temperature of from $0°$ C. to $100°$ C. and basification of the trimethylsulphoxonium hydrogen sulphate formed.

The bis(trimethylsulphonium) sulphate, which may also be used in the epoxidation process, either alone or in combination with trimethylsulphonium hydrogen sulphate is a known compound and may be prepared as described in Z. Kristallog., 147(3–4), 319–25. It is not, however, known that it can be used for the preparation of epoxides.

Both the bis(trimethylsulphoxonium) sulphate, which may be used in the epoxidation process either alone or in combination with trimethylsulphoxonium hydrogen sulphate, and the bis(trimethylsulphonium) sulphate, which may be used in the epoxidation process either alone or in combination with trimethylsulphonium hydrogen sulphate, may occur as impurities during preparation of their respective mono salts.

In the epoxidation process, the carbonyl compound is conveniently added with an organic solvent, for example, toluene, acetonitrile, dichloromethane, polyethylene glycol, methanol, 1,4-dioxane, cyclohexane, n-propanol, n-propanol/toluene, diethylene glycol dimethyl ether (diglyme) or t-butanol, to a solution of trimethylsulphonium hydrogen sulphate, freshly prepared as described above, and the base added gradually while maintaining the temperature between $+10°$ C. and $+100°$ C., preferably at about $40°$ C. The base is suitably a strong base, for example, an alkali metal hydroxide, such as sodium or potassium hydroxide. Potassium hydroxide flake is particularly convenient to use. Typically, 1 to 2 moles of trimethylsulphonium hydrogen sulphate, preferably 1 to 1.2 moles, are used for each mole of carbonyl compound, with typically 1 to 20 moles, preferably 1 to 8 moles of base. The progress of reaction may be monitored by analysing samples taken at intervals using chromatographic methods and the reaction continued until adjudged complete.

The epoxide may be recovered from the reaction mixture by adding water to the mixture, filtering off any residual inorganic salts, distilling off excess dimethyl sulphide and any solvent, such as dichloromethane, used to wash the filtered residues and separating the product as an oil from the aqueous layer.

Trimethylsulphonium hydrogen sulphate can be substituted in the above epoxidation reaction by bis(trimethylsulphonium) sulphate or trimethylsulphoxonium hydrogen sulphate and/or bis(trimethylsulphoxonium) sulphate using the same or similar reaction conditions.

The base can be aqueous or non-aqueous. Aqueous reaction conditions are described in Journal of Organic Chemistry 34, No 7, p2133, 1969.

The reaction can also be carried out using a phase transfer catalyst, such as quaternary ammonium salts, for example, benzyl triethyl ammonium chloride. Suitable conditions for such reactions are given in Indian Patent No. 155768.

The process for preparing the epoxide is believed to proceed via the sulphonium ylide, $(CH_3)_2S^+\text{—}^-CH_2$, which is formed on basification of the trimethylsulphonium hydrogen sulphate, or via the sulphoxonium ylide $(CH_3)_2S^+(O)\text{—}^-CH_2$, which is formed on basification of the trimethylsulphoxonium hydrogen sulphate. These are the same species formed in known processes involving the use of trimethylsulphonium methyl sulphate and trimethylsulphoxonium methyl sulphate to prepare epoxides. The invention is, therefore, applicable to any carbonyl compound which can be transformed into its corresponding epoxide by the sulphonium ylide $(CH_3)_2S^+\text{—}^-CH_2$ or sulphoxonium ylide $(CH_3)_2S^+(O)\text{—}^-CH_2$. This includes any aldehyde or ketone whose transformation to the corresponding epoxide via the sulphonium ylide or sulphoxonium ylide is described in the literature. Of particular interest are ketones of the formula (I) in which $R^1$ is $C_{1-6}$ alkyl, $C_{1-4}$ haloalkyl, $C_{3-6}$ cycloalkyl, $C_{3-6}$ cycloalkyl($C_{1-4}$)alkyl or optionally substituted phenyl; $R^2$ is H, $C_{1-6}$ alkyl, $C_{1-4}$ haloalkyl, $C_{3-6}$ cycloalkyl, $C_{3-6}$ cycloalkyl($C_{1-4}$)alkyl, optionally substituted phenyl or optionally substituted benzyl; or $R^1$ and $R^2$ join together to form a $C_{5-7}$ cycloalkyl ring.

When $R^1$ or $R^2$ is haloalkyl or haloalkoxy, the halogen is preferably fluorine, chlorine or bromine. Substituents which may be present in phenyl groups include one or more of halogen (especially chlorine and fluorine), $C_{1-4}$ alkyl (especially methyl and ethyl), $C_{1-4}$ haloalkyl (especially trifluoromethyl), $C_{1-4}$ alkoxy (especially methoxy and ethoxy), $C_{1-4}$ haloalkoxy (especially trifluoromethoxy and difluoromethoxy), nitro and phenoxy.

Of more particular interest are the compounds of formula (I) in which $R^1$ is n- or t-butyl, trifluoromethyl or phenyl, and $R^2$ is phenyl or benzyl, the phenyl groups and the phenyl moiety of the benzyl group being optionally substituted with fluorine and/or chlorine in the 2- and/or 4-position of the phenyl ring, or with methoxy or ethoxy in the 4-position and optionally fluorine in the 3- and 5-position of the phenyl ring. Specific examples of ketones which are of particular interest are 1-(2,4-dichlorophenyl)-n-pentan-1-one, benzaldehyde, benzophenone, 4-phenyl-2-butanone, 3-methyl-2-butanone, p-ethoxytrifluoro-acetophenone, p-methoxytrifluoro-acetophenone, 3,5-difluoro-4-ethoxytrifluoro-acetophenone, 2,4'-difluorobenzophenone, and 1-(2-chlorophenyl)-3,3-dimethylbutan-2-one.

Such ketones are transformed into epoxides of the formula (II) in which $R^1$ and $R^2$ have the meanings given above.

In a further aspect, the invention provides a process for transforming an aldehyde or ketone into its corresponding epoxide, which comprises either:

(a) reacting together dimethyl sulphide, methanol and concentrated sulphuric acid at a temperature of from $-20°$ C. to $+100°$ C. (in sealed system) or $-20°$ C. to $+40°$ C. (at atmospheric pressure), or (b) reacting together dimethyl sulphide, trimethylsulphonium methyl sulphate and concentrated sulphuric acid at a temperature of from −20° C. to +100° C. (in sealed system) or −20° C. to +40° C. (at atmospheric pressure); or (c) reacting together a trimethylsulphonium halide, sulphuric acid and hydrogen peroxide at a temperature of from 0° C. to 100° C.; or (d) reacting together a trimethylsulphoxonium halide, sulphuric acid and hydrogen peroxide at a temperature of from 0° C. to 100° C.; and contacting the aldehyde or ketone with the product obtained from step (a), (b), (c) or (d) in the presence of a base.

The epoxides obtained by the invention may be useful products in their own right or may be used as intermediates for further processing. For example, the epoxides of formula (II), defined above, may be used to prepare fungicidal compounds of formula (III) in which $R^1$ and $R^2$ have the meanings given above, by reacting the epoxides with 1,2,4-triazole in the presence of a base, such as potassium carbonate.

Thus in a further aspect of the invention there is provided a process for preparing a compound of formula (III) wherein $R^1$ is $C_{1-6}$ alkyl, $C_{1-4}$ haloalkyl, $C_{3-6}$ cycloalkyl, $C_{3-6}$ cycloalkyl($C_{1-4}$)alkyl or optionally substituted phenyl; $R^2$ is H, $C_{1-6}$ alkyl, $C_{1-4}$ haloalkyl, $C_{3-6}$ cycloalkyl, $C_{3-6}$ cycloalkyl($C_{1-4}$)alkyl, optionally substituted phenyl or optionally substituted benzyl; or $R^1$ and $R^2$ join together to form a $C_{5-7}$ cycloalkyl ring; which comprises the steps of (i) either: (a) reacting together dimethyl sulphide, methanol and concentrated sulphuric acid at a temperature of from −20° C. to +100° C. (in a sealed system) or from −20° C. to +40° C. (at atmospheric pressure), or (b) reacting together dimethyl sulphide, trimethyl-sulphonium methyl sulphate and concentrated sulphuric acid at a temperature of from −20° C. to +100° C. (in a sealed system) or from −20° C. to +40° C. (at atmospheric pressure); or (c) reacting together a trimethylsulphonium halide, sulphuric acid and hydrogen peroxide at a temperature of from 0° C. to 100° C.; or (d) reacting together a trimethylsulphoxonium halide, sulphuric acid and hydrogen peroxide at a temperature of from 0° C. to 100° C.; and (ii) transforming a compound of formula (I) wherein $R^1$ and $R^2$ have the meanings given above, into its corresponding epoxide by contacting the compound of formula (I) with the product obtained from step (i) (a), (b), (c) or (d) in the presence of a base; and (iii) reacting the epoxide formed in step (ii) with a 1,2,4-triazole in the presence of a base.

Specific examples of fungicides of formula (III) of interest are 1-(2-fluorophenyl)-1-(4-fluorophenyl)-1-H-1,2,4-triazole-1-ethanol, 1-n-butyl-1-(2,4-dichlorophenyl)-1H-1,2,4-triazole-1-ethanol and those compounds disclosed in EP 15756-A.

The process for the preparation of the epoxide formula (II) is also useful for the preparation of insecticides such as those disclosed in GB 2178739. Particular compounds of interest for transformation to the epoxide are those of formula (I) where $R^1$ is $C_{1-4}$ haloalkyl and $R^2$ is optionally substituted phenyl. The halogen is preferably fluorine or chlorine, and substituents which may be present in the phenyl group include one or more of halogen (especially chlorine, bromine or fluorine), $C_{1-4}$ alkyl (especially methyl and ethyl), $C_{1-4}$ haloalkyl (especially trifluoromethyl), $C_{1-4}$ alkoxy (especially methoxy and ethoxy), $C_{1-4}$ haloalkoxy (especially trifluoromethoxy and difluoromethoxy), nitro and phenoxy.

Of more particular interest are the compounds of formula (I) in which $R^1$ is trifluoromethyl and $R^2$ is phenyl optionally substituted with methoxy or ethoxy in the 4-position and optionally fluorine in the 3- and 5-position of the phenyl ring. Specific examples of ketones which are of particular interest are p-ethoxytrifluoro-acetophenone, p-methoxytrifluoro-acetophenone, 3,5-difluoro-4-ethoxytrifluoro-acetophenone.

The invention is illustrated by the following Examples in which percentages are by weight and the following abbreviations are used: GC=gas chromatography; NMR=nuclear magnetic resonance; s=singlet; m=multiplet; g=grammes; ml=milliliters; THF=tetrahydrofuran; MeOH=methanol; $CDCl_3$=deuterochloroform; DSS=2,2-dimethyl-2-silapentane-5-sulphonate; NMR data are selective. Chemical shifts (δ) are measured in parts per million from TMS or DSS, and $CDCl_3$ or fully deuterated DMSO were used as solvents.

EXAMPLE 1

Preparation of Trimethylsulphonium Hydrogen Sulphate.

Trimethylsulphonium iodide (9.8 g, 0.048 moles) was dissolved in water (50 ml). Sulphuric acid (4.8 g at 98%, 0.048 moles) and hydrogen peroxide (2.72 g at 30%, 0.024 moles) were each diluted to 10 ml with water and added to the stirred trimethylsulphonium iodide solution. Carbon tetrachloride (150 ml) was added to extract the iodine that was produced and the mixture was stirred for 6 hours. The layers were separated. To the aqueous layer was added carbon tetrachloride (150 ml) and this was stirred overnight. The layers were separated and the aqueous layer was extracted with aliquots of carbon tetrachloride (20 ml) until no further pink colouration was visible. Palladium on carbon (3%, 0.25 g) was added to the aqueous solution to destroy any unreacted peroxide. The solution was filtered after 60 minutes, and washed with ether (2×20 ml). The water was removed under reduced pressure to produce an oily residue which was dried under vacuum at 78° C. The oil was dissolved in hot ethanol and cooled in an acetone/solid carbon dioxide bath to produce a white solid. The solid was filtered maintaining the temperature below 0° C. and dried under reduced pressure at 78° C. to yield a very deliquescent residue (2.7 g, 32% yield of theory). This material was dissolved in hot ethanol and allowed to cool slowly in an acetone/solid carbon dioxide bath to produce a waxy solid. The solid was filtered maintaining the temperature below 0° C. and dried under reduced pressure at 80° C. to yield a very deliquescent solid.

Melting point 20°–21° C.; $C_3H_{10}S_2O_4$ (174.2): calculated C 20.7, H 5.8, S 36.8; found C 20.7, H 5.9, S 36.6. $^1$H NMR (DMSO-$d_6$/TMS): δ 2.91(s, 9H, $CH_3$—S); 7.4–7.6(s, 1H, $HSO_4$). pH=1.8–1.9 ($HSO_4^-$).

EXAMPLE 2

Preparation of Trimethylsulphonium Hydrogen Sulphate

Sulphuric acid (23.7 g at 98%, 0.237 moles) was added dropwise over 60 minutes, with stirring, to dimethyl sulphide (20.0 g at 98%, 0.316 moles) while maintaining the temperature below 25° C. Methanol (5.0 g, 0.156 moles) was slowly added to the stirred mixture maintaining the temperature below 30° C. The reaction mixture was stirred for 5 hours at room temperature then held unagitated over the weekend. Two layers were present. The upper layer was excess dimethylsulphide and the lower aqueous layer contained trimethylsulphonium hydrogen sulphate and excess sulphuric acid. The lower aqueous layer was separated off for analysis by titration. (For subsequent use of this complete reaction mixture in epoxidation reactions.

Using a non-aqueous titration system (THF/MeOH as solvent, tetrabutyl ammonium hydroxide as base), it was shown that the aqueous layer of the reaction mixture (prior to its use in the epoxidation reaction) contained a mixture of sulphuric acid and hydrogen sulphate ions ($HSO_4^-$).

EXAMPLE 3

Preparation of Bis(trimethylsulphonium) Sulphate

Silver sulphate (7.0 g, 0.022 mole) was dissolved in water (1200 ml) at room temperature. Trimethylsulphonium iodide (9.16 g, 0.045 mole) was dissolved in water (50 ml) and added to the stirred silver sulphate solution. The reaction mixture was stirred for 3 hours at room temperature during which time a solid (silver iodide) was precipitated. This solid was filtered off and the filtrates concentrated under reduced pressure to leave a grey solid. The grey solid was slurried in methanol and insoluble material removed by filtration. The methanol filtrates were concentrated under reduced pressure to leave a white solid. This solid was recrystallized from acetone, then from a methanol/ethanol mixture and dried under vacuum at 78° C. to give a white hygroscopic solid.

$C_6H_{18}O_4S_3$ (250.4): calculated C 28.8, H 7.2, S 38.4; found C 28.5, H 7.2, S 38.7; $^1$HNMR ($D_2O$,DSS): δ 2.9 (s, $CH_3$—S); pH=7.4 (0.02M solution)

EXAMPLE 4

Preparation of 1-(2,4-dichlorophenyl)-1-n-butyloxirane

Trimethylsulphonium hydrogen sulphate (prepared by the method described in Example 1) (2.0 g, 0.0115 mole) was added to dimethylsulphide (0.73 g, 0.0117 mole) and t-butanol (0.26 g, 0.0035 mole). Water (0.2 g, 0.011 mole) and 1-(2,4-dichlorophenyl)-n-pentan-1-one (2.7 g at 95.5%, 0.011 mole) was added and the mixture stirred vigorously. Potassium hydroxide flake (3.2 g, 0.054 mole) was added to the mixture and stirred at room temperature for 3 hours. A sample was removed for analysis by GC and this showed 94% conversion to the title epoxide by comparison with an authentic sample.

The NMR characteristics of the authentic sample are: $^1$HNMR ($CDCl_3$, TMS): δ 0.5–2.4 (m, 9H, $(CH_2)_3CH_3$); 2.6–3.0 (m, 2H, $CH_2O$), 7.0–7.5 (m, 6H, aromatic H).

EXAMPLE 5

Preparation of 1,2-epoxyethylbenzene

Sulphuric acid (23.7 g at 98%, 0.237 moles) was added dropwise, with stirring, to dimethylsulphide (20.0 g at 98%, 0.316 moles) over 60 minutes, maintaining the temperature below 30° C. Methanol (5.0 g, 0.156 moles) was added over 30 minutes to the stirred mixture, maintaining the temperature below 35° C. The reaction mixture was stirred for 4½ hours and held overnight unagitated at room temperature.

To the stirred mixture was added t-butanol (3.6 g, 0.048 moles). Potassium hydroxide flake (34.0 g, 0.58 mole) was added in 10 equal aliquots over 2½ hours. Benzaldehyde (15.9 g, 0.15 mole) was added after the seventh potassium hydroxide aliquot and an alkaline pH had been achieved. After stirring overnight at room temperature, analysis by GC indicated the presence of unreacted benzaldehyde. A further aliquot of potassium hydroxide (3.4 g, 0.058 mole) was added and the reaction mixture stirred for a further 4 hours.

The reaction mixture was added to water (600 ml) and extracted with pentane (5×20 ml). The pentane extracts were combined and the solvent removed under reduced pressure to give a yellow oil. The oil was distilled under reduced pressure (7 mm Hg, still head temperature 64°–65° C.) to give a clear colourless oil, (10.6 g, 55% yield of theory).

$^1$H NMR ($CDCl_3$/TMS): δ=2.6–3.15 (m, 2H, $CH_2$—O); 3.65–3.9 (m, 1H, CH—O); 7.1–7.5 (m, 5H, aromatic H). (Spectrum identical to that of authentic sample).

EXAMPLE 6

Preparation of 1,1-diphenyl-1,2-epoxyethane

Sulphuric acid (23.7 g at 98%, 0.237 moles) was added dropwise, with stirring, to dimethylsulphide (20.0 g at 98%, 0.316 moles) over 60 minutes, maintaining the temperature below 26° C. Methanol (5.0 g, 0.156 mole) was added slowly to the stirred mixture maintaining the temperature below 31° C. The reaction mixture was stirred for 4½ hours and held overnight unagitated at room temperature. Tertiary butanol (3.6 g, 0.048 mole) and benzophenone (27.4 g, 0.15 mole) were added to the reaction mixture. Potassium hydroxide flake (43.4 g, 0.73 mole) was added in 10 equal aliquots over 3 hours while maintaining the temperature below 40° C. The reaction was monitored by GC and then stirred overnight at room temperature.

The reaction mixture was poured into water (1000 ml) to dissolve the inorganic material, and extracted with diethyl ether (3×100 ml). The combined ether extracts were dried over anhydrous sodium sulphate, filtered and the solvent removed under reduced pressure to yield a white solid which was recrystallised from ethanol (15.7 g, 52% yield of theory).

$^1$H NMR (DMSO-$d_6$/DSS): δ=3.28 (s, 2H, $CH_2$—O), 7.35 (s, 10H, aromatic H).

EXAMPLE 7

Preparation of (1-(4-ethoxyphenyl)-1-trifluoromethyl oxirane

Trimethylsulphoxonium iodide (22 g, 0.1 moles) was dissolved in water (133 ml). Sulphuric acid (10 g at 98%, 0.1 moles) and hydrogen peroxide (5.7 g at 30%, 0.05 moles) were then added to the stirred trimethylsulphoxonium iodide solution. Carbon tetrachloride (600 g) was added to extract the iodine that was produced and the mixture was stirred for 16 hours. The mixture was filtered to remove any solids and the layers were then separated. The aqueous layer was washed with carbon tetrachloride (2×500 mls) and iodine was still being extracted. Therefore, carbon tetrachloride (600 ml) was added to the aqueous layer, stirred for one hour and the layers separated. Further washing of the aqueous layer with carbon tetrachloride (50 ml) showed no colour change indicating that the iodine had been completely extracted. The aqueous layer was washed with ether (50 ml) and sodium metabisulphite (0.2 g) was added to destroy any residual hydrogen peroxide.

To the stirred aqueous layer was added sodium hydroxide (8.6 g at 98%, 0.211 moles) and cyclohexane (21.9 g, 0.26 moles). The mixture was heated to 55° C. and stirred for 40 minutes. p-Ethoxytrifluoroacetophenone (22.4 g at 97.5%, 0.1 moles) was added dropwise over 40 minutes and the reaction mixture stirred at 55° C. for 22 hours. Cyclohexane (30 ml) was added to the mixture and the layers separated. The organic layer was washed with water (3×100 ml) and then concentrated under reduced pressure to give a yellow oil (22.1 g). Quantitative analysis by GC showed 85% strength of the title epoxide, i.e. 81% yield of theory.

$^1$H NMR (CDCl$_3$/TMS): δ 1.2–1.5 (t, 3H, CH$_3$), 2.3–3.5 (m, 2H, CH$_2$—O epoxide) 3.9–4.2 (q, 2H, CH$_2$—CH$_3$), 6.8–7.6 (m, 4H; aromatic H)

EXAMPLE 8

Preparation of 1,2-epoxy-2-methyl-4-phenylbutane

Using the same conditions described in Example 5, but using dichloromethane as the extraction solvent, 4-phenyl-2-butanone (22.2 g, 0.15 mole) yielded an orange oil; 1,2-epoxy-2-methyl-4-phenylbutane (19.8 g, 72% yield of theory).

$^1$H NMR (CDCl$_3$/TMS): δ 1.3(s,3H, CH$_3$); 1.6–2.1(m, 2H), 2.4–2.8(m, 4H); 6.8–7.4(m, 5H, aromatic H).

EXAMPLE 9

Preparation of 2,3-dimethyl-1,2-epoxybutane

Using the same conditions described in Example 5, but using dichloromethane as the extraction solvent, 3-methyl-2-butanone (12.9 g, 0.15 mole) gave 2,3-dimethyl-1,2-epoxybutane (8.0 g, 47% yield of theory).

$^1$H NMR (CDCl$_3$/TMS): δ 0.8–1.1(m, 6H, CH$_3$—CH); 1.1.–1.6(m, 4H, CH$_3$—C and C—H); 2.6(m, 2H, CH$_2$—O).

EXAMPLE 10

Preparation of 1-oxaspiro[2,5]octane.

Under the same conditions described in Example 5, cyclohexanone (14.7 g, 0.15 mole) yielded a pale yellow/green oil, 1-oxaspiro[2,5]octane (10.5 g, 55% yield of theory);

$^1$H NMR(DMSO-d$_6$/TMS): δ 1.0–2.0(m, ring CH$_2$); 2.4–2.6(m, CH$_2$—O).

| $^{13}$C—NMR(DMSO-d$_6$/TMS): | δ ppm | C number |
|---|---|---|
| (see (IV) for ring numbering) | 24.4 | 3, 5 |
|  | 24.7 | 4 |
|  | 33.1 | 2, 6 |
|  | 52.9 | 7 |
|  | 57.7 | 1 |

EXAMPLE 11

Preparation of 1-(2,4-dichlorophenyl)-1-n-butyl oxirane

Bis(trimethylsulphonium)sulphate (0.85 g, 3.4 mmole) (prepared by the method described in Example 3) was added to dimethylsulphide (0.43 g, 6.9 mmole) and t-butanol (0.15 g, 2 mmole). Water (0.12 g, 7 mmole) and 1-(2,4-dichlorophenyl)-n-pentan-1-one (1.57 g at 95.5%, 6.5 mmole) were added and the mixture stirred vigorously. Potassium hydroxide flake (1.07 g at 95%, 18 mmole) was then added and the mixture stirred at ambient temperature for 50 hours.

Water was added to the reaction mixture to dissolve any inorganic material and the mixture extracted with dichloromethane. The dichloromethane extracts were concentrated under reduced pressure to leave an oil (1.37 g, % area of epoxide by GC=97.9%, 86% yield of theory by comparison with the authentic sample given in Example 4).

EXAMPLE 12

Preparation of 1-(2,4-dichlorophenyl)-1-n-butyl oxirane.

Methanol (13.4 g, 0.419 moles) was added dropwise over 10 minutes to dimethylsulphide (52.1 g, 0.841 moles) while maintaining the temperature below 25° C. Sulphuric acid (46.2 g at 98%, 0.462 moles) was added to the stirred mixture over 30 minutes maintaining the temperature below 25° C. The reaction mixture was stirred overnight at room temperature. 1-(2,4-Dichlorophenyl)-n-pentan-1-one (92.4 g, 0.4 mole) and t-butanol (9.4 g, 0.127 moles) were added with stirring to the reaction mixture. Potassium hydroxide flake (100.7 g, 1.7 moles) was added portionwise while maintaining the temperature at 40° C. over 6 hours. During the addition the reaction was monitored by GC.

Water (250 ml) was added and the reaction mixture filtered to remove potassium sulphate. The filter cake was washed with water (250 ml) and dichloromethane (100 ml). The combined filtrates were charged to a separating funnel and the lower organic layer removed and transferred to a flask, containing water (100 ml), set up for atmospheric distillation. Dichloromethane and dimethyl sulphide were removed by distillation (final pot temperature; 90° C.). The remaining reaction mixture was transferred to a separating funnel and the lower product layer separated off as a light brown oil (96.4 g, 56.1% strength—53% yield of theory by comparison with the authentic sample given in Example 4).

This reaction was repeated using higher levels of acid. The results are given in Table I.

TABLE I

| Mole Ratios | | | Penta- | Product % Penta- | Strength % | Yield of |
|---|---|---|---|---|---|---|
| (CH$_3$)$_2$S | CH$_3$OH | H$_2$SO$_4$ | none | none | Epoxide | Epoxide |
| 2.1 | 1.0 | 1.7 | 1.0 | 8.6 | 82.5 | 79.0 Note 1 |
| 2.1 | 1.0 | 1.7 | 0.8 | 0.1 | 87.2 | 92.0 Note 2 |

Notes
1. The sulphuric acid was added before the methanol in this experiment. The potassium hydroxide was added more quickly (over 2½ hours). The reaction mixture was then stirred for 4 hours at room temperature.
2. The sulphuric acid was added before the methanol in this experiment. The potassium hydroxide was added over 3 hours at room temperature.

Notes

1. The sulphuric acid was added before the methanol in this experiment. The potassium hydroxide was added more quickly (over 2½ hours). The reaction mixture was then stirred for 4 hours at room temperature.

2. The sulphuric acid was added before the methanol in this experiment. The potassium hydroxide was added over 3 hours at room temperature.

EXAMPLE 13

Preparation of 1-(2,4-dichlorophenyl)-1-n-butyl oxirane.

Dimethyl sulphide (3.6 g, 0.058 moles) was added to a solution of trimethylsulphonium methyl sulphate (5.97 g, 0.029 moles) in water (0.5 ml). Sulphuric acid (5.8 g at 98%, 0.058 moles) was added dropwise, with stirring, to the mixture. The mixture was heated to 40° C. and stirred for 6 hours before being stopped and left unagitated overnight. The following is an NMR characterisation of the reaction mixture demonstrating that only a trace of CH$_3$SO$_4^-$ remained after the reaction.

1H NMR (DMSO d$_6$/DSS): δ 2.0 (singlet, integration=10, (CH$_3$)$_2$S); 3.0 (singlet, integration=130, (CH$_3$)$_3$S$^+$); 3.5 (singlet, integration=1, CH$_3$SO$_4^-$).

1-(2,4-Dichlorophenyl)-n-pentan-1-one (12.76 g, 0.055 moles) and t-butanol (4.1 g, 0.055 moles) were added to the stirred mixture. Potassium hydroxide flake (15.4 g, 0.275 moles) was added portionwise over 1 hour and the mixture was stirred at room temperature for 3 hours. The reaction mixture was then left unagitated over the weekend.

Water (50 ml) was added and apparatus set up for atmospheric distillation. Dimethyl sulphide was removed by distillation up to a column head temperature of 55° C. Water was added (>250 ml) to dissolve all inorganic salts and the layers allowed to separate. The lower epoxide layer was separated off and washed with water (50 ml). The aqueous layer was extracted with dichloromethane and the dichloromethane removed on the rotary evaporator. Total weight of epoxide obtained: 11.15 g; % area of epoxide by CC: 88%; yield of epoxide: 72.8% (by comparison with the authentic sample given in Example 4).

EXAMPLE 14

Preparation of 1,2-epoxyethylbenzene

Sulphuric acid (15 g at 98%, 0.15 moles) was added dropwise over 60 minutes, with stirring, to dimethyl sulphide (12.65 g at 98%, 0.2 moles) while maintaining the temperature below 25° C. Methanol (3.2 g, 0.1 moles) was slowly added to the stirred mixture maintaining the temperature below 30° C. The reaction mixture was stirred for 4½ hours.

To the sulphonium salt mixture was added benzaldehyde (13.52 g at 98%, 0.125 moles), toluene (92 g, 1 mole), and n-propanol (35.5 g, 0.59 moles) and the mixture stirred and heated to 50° C. Aqueous sodium hydroxide solution (32 g at 53%, 0.425 moles) was added and a temperature rise to 80° C. was observed (due to neutralisation of excess acid). The mixture was cooled to 70° C. and stirred at this temperature for 1 hour. The mixture was cooled, the organic layer separated, washed with water and dried over magnesium sulphate. Qualitative GC analysis showed 76% conversion to the title epoxide (by comparison with authentic sample).

EXAMPLE 15

Preparation of 1-(2,4-dichlorophenyl)-1-n-butyloxirane

Sulphuric acid (18.75 g at 98%, 0.187 moles) was added dropwise over 60 minutes, with stirring, to dimethyl sulphide, (15.8 g at 98%, 0.25 moles) while maintaining the temperature below 25° C. Methanol (4.0 g, 0.125 moles) was slowly added to the stirred mixture maintaining the temperature below 30° C. The reaction mixture was stirred for 4½ hours.

To the stirred mixture was added dichloromethane (53.5 g, 0.63 moles), 1-(2,4-dichlorophenyl)-n-pentan-1-one (19.35 g at 95.5%, 0.08 moles) and benzyltriethyl ammonium chloride (0.82 g, 0.0036 moles).

Aqueous sodium hydroxide solution (46.3 g, 1.16 moles NaOH in 32 g water) was added to the mixture and stirred for 20 hours at room temperature. Water (350 ml) was added and the layers allowed to settle. The organic layer was separated and the aqueous layer extracted with dichloromethane (4×50 ml). The organic extracts were combined and washed with water until a neutral pH was obtained. The organic layer was then dried over anhydrous sodium sulphate and solvent removed under reduced pressure to yield an oil (20.6 g) at 84.8%, i.e. 89% of theory, by comparison with the authentic sample given in Example 4).

EXAMPLE 16

Preparation of 1-(2,4-dichlorophenyl)-1-n-butyl oxirane

Sulphuric acid (18.75 g at 98%, 0.187 moles) was added dropwise with stirring to dimethyl sulphide (15.8 g at 98%, 0.25 moles) over 60 minutes, maintaining the temperature below 25° C. Methanol (4.0 g, 0.125 moles) was added slowly to the stirred mixture, maintaining the temperature below 30° C. The reaction mixture was stirred for 4½ hours and held unagitated overnight at room temperature.

To the stirred mixture was added t-butanol (2.3 g, 0.032 moles) and 1-(2,4-dichlorophenyl)-n-pentan-1-one (24.2 g at 95.5%, 0.1 moles).

Sodium hydroxide (24.0 g at 98%, 0.59 moles) in the form of pellets was added in 8 aliquots over 3 hours and the mixture then stirred at room temperature overnight.

The reaction mixture was added to water (to dissolve any inorganic material) and extracted with dichloromethane. The dichloromethane layer was separated and the solvent removed under reduced pressure to give an oil (24.3 g at 91.6%, i.e. 90.8% yield of theory, by comparison with the authentic sample given in Example 4).

EXAMPLE 17

Preparation of 1-(2,4-dichlorophenyl)-1-n-butyloxirane

Sulphuric acid (21.2 g at 98%, 0.212 moles) was added dropwise with stirring to dimethylsulphide (16.4 g at 98%, 0.26 moles) over a period of time maintaining the temperature below 25° C. Methanol (4.0 g, 0.125 moles) was added slowly to the stirred mixture, maintaining the temperature below 30° C. The reaction mixture was stirred at 25° C. for 4½ hours and held unagitated overnight at room temperature.

To the stirred mixture was added t-butanol (2.3 g, 0.032 moles) and 1-(2,4-dichlorophenyl)-n-pentan-1-one (24.2 g at 96.5%, 0.1 moles).

Potassium hydroxide flake (34.8 g, 0.59 moles) was added in ten aliquots over 3 hours and the mixture then stirred at room temperature overnight.

The reaction mixture was added to water (to dissolve an inorganic material) and extracted with dichloromethane. The dichloromethane layer was separated and the solvent removed under reduced pressure to give an oil (22.7 g at 87.7%, 81.2% yield of theory, by GC comparison with authentic sample).

The reaction was repeated using different temperatures during the formation of the trimethyl sulphonium hydrogen sulphate. The results are given below.

| Temperature °C. | Yield of epoxide % |
| --- | --- |
| −20 | 75.9 |
| 0 | 74.9 |
| 40 | 82.0 |

CHEMICAL FORMULAE
(corresponding to formulae numbers given in the description)

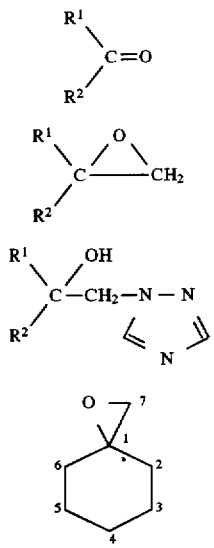

We claim:

1. A process for transforming an aldehyde or ketone into its corresponding epoxide, which comprises a first step selected from the group of processes consisting of:
   (a) reacting together dimethyl sulphide, methanol and concentrated sulphuric acid at a temperature of from −20° C. to +100° C. (in a sealed system) or from −20° C. to +40° C. (at atmospheric pressure); and
   (b) reacting together a trimethylsulphonium halide, sulphuric acid and hydrogen peroxide at a temperature of from 0° C. to 100° C.;

and then reacting the aldehyde or ketone with the product obtained from said first step in the presence of a base.

2. A process according to claim 1 wherein the base is an alkali metal hydroxide.

3. A process according to claim 1 wherein said first step is process (a) in which concentrated sulphuric acid is added to a stirred mixture of methanol and dimethyl sulphide.

4. A process according to claim 1 wherein said first step is process (b) in which the trimethylsulphonium halide is trimethylsulphonium iodide and an inert, water immiscible, iodine-extracting solvent is present.

5. A process for transforming a carbonyl compound of the formula (I):

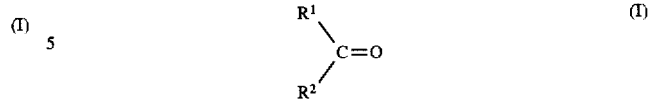

into its corresponding epoxide of formula (II):

wherein $R^1$ is $C_{1-6}$ alkyl, $C_{1-4}$ haloalkyl, $C_{3-6}$ cycloalkyl, $C_{3-6}$ cycloalkyl($C_{1-4}$)alkyl, phenyl or substituted phenyl; $R^2$ is H, $C_{1-6}$ alkyl, $C_{1-4}$ haloalkyl, $C_{3-6}$ cycloalkyl, $C_{3-6}$ cycloalkyl($C_{1-4}$)alkyl, phenyl, substituted phenyl, benzyl or substituted benzyl; wherein substituents present in said substituted phenyl and benzyl groups are selected from the group consisting of halogen, $C_{1-4}$ alkyl, $C_{1-4}$ haloalkyl, $C_{1-4}$ alkoxy, $C_{1-4}$ haloalkoxy, nitro and phenoxy; or $R^1$ and $R^2$ join together to form a $C_{5-7}$ cycloalkyl ring; the process comprising:

i) preparing trimethylsulphonium hydrogen sulphate by
      (a) reacting dimethyl sulphide, methanol and concentrated sulphuric acid at a temperature of from −20° C. to +100° C. (in a sealed system) or from −20° C. to +40° C. (at atmospheric pressure); or
      (b) reacting a trimethylsulphonium halide, sulphuric acid and hydrogen peroxide at a temperature of from 0° C. to 100° C.; and ii) reacting the carbonyl compound with the product obtained from step (a) or (b) in the presence of a base.

6. A process according to claim 5 wherein the base is an alkali metal hydroxide.

7. A process according to claim 5 wherein in step i)(a) concentrated sulfuric acid is added to a stirred mixture of methanol and dimethyl sulphide.

8. A process according to claim 5 wherein in step i)(b) the trimethylsulphonium halide is trimethylsulphonium iodide and an inert, water immiscible, iodine-extracting solvent is present.

* * * * *